(12) United States Patent
Woo et al.

(10) Patent No.: US 6,761,736 B1
(45) Date of Patent: Jul. 13, 2004

(54) MEDICAL ARTICLE WITH A DIAMOND-LIKE CARBON COATED POLYMER

(75) Inventors: Yi-Ren Woo, Woodbury, MN (US); Avrom M. Brendzel, Roseville, MN (US); Chad Qingshen Cai, Woodbury, MN (US); Stephen A. Peterson, Lincoln, RI (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/437,167

(22) Filed: Nov. 10, 1999

(51) Int. Cl.[7] ................................................. A61F 2/24
(52) U.S. Cl. ..................... 623/2.42; 623/2.12; 623/1.46
(58) Field of Search ............................ 623/1.46, 1.49, 623/1.54, 1.44, 2.12, 2.42; 606/190, 194, 198, 200; 528/397

(56) References Cited

U.S. PATENT DOCUMENTS

| | | | |
|---|---|---|---|
| 3,932,627 A | * | 1/1976 | Margraf ........................ 514/56 |
| 3,952,334 A | | 4/1976 | Bokros et al. ........................ 3/1 |
| 4,698,256 A | | 10/1987 | Giglia et al. ................. 428/216 |
| 4,756,964 A | | 7/1988 | Kincaid et al. .............. 428/408 |
| 4,759,759 A | * | 7/1988 | Walker et al. ................... 623/2 |
| 5,346,729 A | * | 9/1994 | Pitts et al. ................... 427/582 |
| 5,370,684 A | * | 12/1994 | Vallana et al. .............. 623/1.46 |
| 5,387,247 A | | 2/1995 | Vallana et al. ................ 623/66 |
| 5,423,886 A | | 6/1995 | Arru et al. ....................... 623/1 |
| 5,455,081 A | | 10/1995 | Okada et al. ................ 427/528 |
| 5,516,884 A | * | 5/1996 | Bianconi ..................... 528/397 |
| 5,632,779 A | * | 5/1997 | Davidson ..................... 623/12 |
| 5,725,573 A | | 3/1998 | Dearnaley et al. .............. 623/2 |
| 5,925,063 A | * | 7/1999 | Khosravi ..................... 606/200 |
| 5,945,153 A | | 8/1999 | Dearnaley .................. 427/2.12 |
| 5,984,905 A | * | 11/1999 | Dearnaley .................. 623/1.46 |

FOREIGN PATENT DOCUMENTS

| | | |
|---|---|---|
| EP | 0 302 717 | 2/1989 |
| EP | 0 302 717 A1 | 2/1989 |
| EP | 0 876 821 A2 | 11/1998 |
| GB | 2 287 473 A | 9/1995 |
| JP | 59-192366 | 10/1984 |
| JP | 60-135062 | 7/1985 |

* cited by examiner

*Primary Examiner*—Cary E. O'Connor
(74) *Attorney, Agent, or Firm*—Altera Law Group, LLC; Hallie A. Finucane (57) ABSTRACT

Implantable vascular devices and implantable cardiovascular devices suitable for contacting a patient's blood or bodily fluids include a polymer substrate that is at least partly coated with a diamond-like carbon coating. The diamond-like carbon coated polymer substrate can be flexible or rigid. Preferred medical devices include heart valve prostheses with leaflets or orifice rings formed from diamond-like carbon coated polymer materials. Preferred approaches for the deposition of the diamond-like carbon coating are performed at low pressures and include ion beam assisted deposition.

29 Claims, 2 Drawing Sheets

MEDICAL ARTICLE WITH A DIAMOND-LIKE CARBON COATED POLYMER

BACKGROUND OF THE INVENTION

The invention relates to medical articles that include substrates having a diamond-like carbon coating. More particularly, the invention relates to medical articles including a polymer material with a diamond-like carbon coating.

A variety of medical articles are designed particularly for contact with a patient's bodily fluids. The duration of this contact may be relatively short, as is typical with wound dressings, burn dressings and contact lenses, or may be long term, as is typical with implanted prostheses, such as prosthetic heart valves implanted into the body of a recipient. Some articles, such as catheters, can have either short term or relatively long term contact.

Prostheses, i.e., prosthetic articles, are used to repair or replace damaged or diseased organs, tissues and other structures in humans and animals. Prostheses generally must be biocompatible since they are typically implanted for extended periods of time. Physicians use a variety of prostheses to correct problems associated with the cardiovascular system, especially the heart. For example, the ability to replace or repair diseased heart valves with prosthetic devices has provided surgeons with a method of treating heart valve deficiencies due to disease and congenital defects. A typical procedure involves removal of the native valve and surgical replacement with a mechanical or bioprosthetic, i.e., tissue based, valve. Another technique uses an annuloplasty ring to provide structural support to the natural annulus of the native valve.

Many biocompatible medical devices and/or their components have important requirements with respect to their mechanical and physical properties. For example, the medical devices are often limited in their size. At the same time, the devices and/or their components may be subjected to demanding structural requirements, such as mechanical strength and long term wear requirements. Thus, there are significant restraints imposed on the design of many medical devices and/or their components.

As a particular example, prosthetic heart valve leaflets or occluders perform the function of opening and closing to regulate the blood flow through the heart valve. Typically, heart valve leaflets must either pivot or flex with each cycle of the heart to open and close. Leaflets in purely mechanical heart valve prostheses generally pivot to open and close the valve. In bioprostheses, flexible leaflets are designed to approximate natural leaflet function. While these leaflets are flexible, they must have a well defined and stable configuration to properly close the valve at each cycle to reduce back flow. Also, the leaflets should be durable to provide stable performance over many years of use.

Conventional bioprostheses use tissue that has been appropriately processed. For example, a natural allograft or xenograft heart valve can be processed to produce a heart valve prosthesis. While tissue leaflets have desired flexibility and acceptable hemodynamic performance, tissue leaflets can calcify after implantation, which results in loss of flexibility resulting in improper closure or opening of the valve.

SUMMARY OF THE INVENTION

In a first aspect, the invention pertains to a medical article suitable for contact with a patient's blood, the medical article comprising a polymer substrate at least a portion of which is coated with a diamond-like carbon coating, the medical article being an implantable vascular device or an implantable cardiovascular device.

In a further aspect, the invention pertains to a method of making a medical article including applying a diamond-like carbon coating onto a polymer substrate and forming at least a portion of a medical article from the diamond-like carbon coated polymer substrate. The diamond-like carbon coating is preferably applied using ion beam assisted deposition. In some embodiments, the polymer substrate degrades at a temperature no more than about 200° C., and in particular embodiments less than about 150° C., and the application is performed under conditions at which the polymer substrate is not significantly structurally or chemically degraded.

In another aspect, the invention pertains to a heart valve prosthesis comprising at least one leaflet that is located along the flow path through the valve, in which the at least one leaflet can move to alter the amount of flow through the valve, the leaflet comprising a polymer substrate at least partially coated with diamond-like carbon.

In an additional aspect, the invention pertains to a medical article suitable for contact with a patient's bodily fluids, the medical article comprising a polymer substrate, for example in selected flexible embodiments, at least a portion of which is coated with a diamond-like carbon coating, the polymer substrate having a thickness less than about 600 microns.

DETAILED DESCRIPTION OF THE PREFERRED EMBODIMENTS

The performance characteristics of certain medical articles that contact a patient's bodily fluids can be improved when the article or components of the medical article have a polymer substrate with a diamond-like carbon coating. Polymer components can incorporate complex structural features and a desirable range of mechanical properties, such as durability, elasticity, fatigue resistance, and compliance. The application of an extremely durable, inert and blood compatible coating over the surface of the polymer greatly expands the useful application of polymers as medical articles or as components of medical articles that contact a patient's bodily fluids or tissues, especially blood. The diamond-like carbon coating provides a barrier that protects the substrate from undesirable reactions with bodily fluids. Such reactions without the protection of the diamond-like carbon coating may reduce the durability of the substrate and/or of the prosthetic device. Generally, the diamond-like carbon coating is applied under conditions that do not significantly degrade the polymer substrate. The diamond-like carbon coated polymer materials combine the desirable versatility of polymer materials with the durability, hardness, inertness and blood compatibility of diamond-like carbon coatings.

A variety of medical articles can be used to contact bodily fluids of a patient. Relevant biocompatible medical articles generally incorporate a biocompatible material which is intended to contact the patient's biological fluids and/or tissues. Bodily fluids include, for example, blood, plasma, serum, interstitial fluids, saliva and urine. The patient can be an animal, especially a mammal, and preferably is a human.

Relevant medical articles include devices that contact a person's bodily fluids for varying lengths of time, for example, prostheses, catheters and surgical instruments. Prostheses, i.e., prosthetic articles, are used to repair or replace damaged or diseased organs, tissues and other structures in humans and animals. Prostheses generally must be biocompatible since they are typically implanted for extended periods of time. Preferred prostheses include prostheses used in the cardiovascular system in which the presence of a diamond-like carbon coating improves the biocompatibility, blood compatibility, lubricity and durability of the prostheses.

Many polymers are biocompatible, in that they are non-toxic, non-carcinogenic and do not induce hemolysis or an immunological responses. Blood contacting medical devices formed from polymers preferably are non-thrombogenic. Polymers are an appealing biocompatible material for use in medical devices that contact bodily fluids since polymer components can incorporate complex structural features and a desirable range of mechanical properties. Mechanical properties of polymers include, for example, stiffness, strength, hardness, fatigue resistance and tear resistance. Furthermore, polymers can be formed into components with a variety of shapes and sizes. For example, flexible polymers can be used to form components, such as valve occluders/leaflets of valved grafts, valved vein grafts or heart valve prostheses. In addition, rigid polymers can be used, for example, to form occluders/leaflets in mechanical heart valve prostheses.

While polymers are versatile with respect to the formation of components for medical devices, polymers in contact with a patient's bodily fluids or tissue can undergo; over time, surface modification, including, for example, degradation, cracking, corrosion, calcification and deposition of blood components, such as proteins or lipids. Surface modification can eventually result in mechanical changes, such as the loss of flexibility and/or loss of structural integrity. Similarly, surface modification can alter the hemodynamic, biocompatibility and durability properties of the device. The application of a diamond-like carbon coating can prevent surface modification without altering desirable mechanical and chemical properties of the polymer substrate.

Carbon has two well characterized crystalline allotropes, diamond and graphite. In addition, amorphous carbon is well known. The strong directional $sp^3$ bonding of diamond gives it many unique properties, such as the highest elastic modulus, hardness and room temperature thermal conductivity of any known solid. In contrast, planar $sp^2$ bonding gives graphite a layered structure with weak interlayer bonding, which makes graphite suitable as a lubricant.

Several different types of carbon coatings can be applied to substrates. Carbon coatings formed by physical vapor deposition, such as sputtering, or by chemical vapor deposition and other thermal processes generally are graphitic carbon. Pyrolytic carbon coatings include polycrystalline graphitic grains throughout the coating. The graphitic nature of the crystalline grains leads to very distinct properties of the resultant coating. While pyrolytic carbon coatings can be biocompatible pyrolytic carbon coatings are not nearly as hard or as inert as diamond-like carbon coatings.

Diamond-like carbon (DLC) films, also known as amorphous carbon-hydrogen films, encompass a range of amorphous carbon structures with a range of $sp^2/sp^3$ bonding ratios and a range of hydrogen concentrations, as described further below. The $sp^3$ bonding component of the diamond-like carbon coatings provides desirable properties for coatings of polymer medical devices or components, which $sp^2$ graphitic bonding, such as found in pyrolytic carbon, can not provide.

Diamond-like carbon coatings are smooth and extremely inert with respect to chemical and biological reactivity. Diamond-like carbon coatings can have a hardness and strength higher than that of graphitic carbon if they are deposited under appropriate conditions and contain suitable amounts of hydrogen, as described further below. In addition, the durability and blood compatibility properties of the component or article can be improved relative to the corresponding polymer components by inhibiting surface modification of the material. Furthermore, the diamond-like carbon coated polymer is less thrombogenic (more blood compatible) than the uncoated polymer.

Typical deposition methods for diamond-like carbon coatings, like magnetron sputtering, heat the substrate to high temperatures. Even if the polymer substrates do not melt or decompose at the corresponding deposition temperatures, the mechanical properties of the polymer substrates can be degraded by subjecting the substrates to these elevated temperatures. Thus, preferred approaches for the deposition of diamond-like carbon are processes that do not result in the heating of the substrate to high temperatures in excess of about 200° C. Preferred approaches include, for example, ion beam assisted deposition and radio-frequency plasma deposition.

When applied to a polymer substrate, diamond-like carbon coatings can form covalent bonds with the polymer substrate. Due to these covalent bonds, the diamond-like carbon coating material is firmly secured to the polymer substrate and will not detach from the polymer. Furthermore, it has been discovered that appropriately deposited diamond-like carbon coatings do not crack when applied to a flexible polymer substrate, even though the diamond-like carbon coating is extremely hard. The DLC coating resists cracking even when the polymer is flexed repeatedly. Similarly, preferred flexible composites of diamond-like carbon on a flexible polymer can be bent significantly, about 100° or more and preferably up to approximately 180° bending, without damage to the coating or loss of adhesion or attachment of the coating to the polymer substrate. In some flexible embodiments, it is desirable that the diamond-like carbon coated polymers can be bent up to 180° with a radius of curvature comparable to or less than the thickness of the substrate, without damage to the coating or loss of adhesion of the coating to the polymer substrate. Thus, diamond-like carbon coatings, when applied using an appropriate method, serve as an extremely stable and durable coating on polymer components of medical devices.

Medical Articles

Relevant biocompatible articles include all medical articles that contact bodily fluids and tissues. These articles can be organized roughly into three groups: implanted devices, percutaneous devices and cutaneous devices. Implanted devices broadly include articles that are fully implanted in a patient, i.e., are completely internal. Percutaneous devices include items that penetrate the skin, thereby extending from outside the body into the body. Cutaneous devices are used superficially, for example, at a wound site or at a moist membrane, such as within a patient's mouth. All of these types of medical articles can incorporate diamond-like carbon coated polymer materials.

Implanted devices include, without limitation, pacemakers, defibrillators, artificial organs such as artificial hearts, ventricular assist devices, anatomical reconstruction prostheses such as breast implants, heart valve prostheses, sewing cuffs for heart valve prostheses, tissue patches such as pericardial patches, surgical patches, coronary stents, vascular grafts and conduits, vascular and structural stents, vascular and cardiovascular shunts, biological conduits, pledgets, sutures, annuloplasty rings, stents, staples, electrical leads such as pacing leads, valved grafts, dermal grafts for wound healing, orthopedic or spinal implants, orthopedic pins, intrauterine devices (IUDs), urinary stents, permanently indwelling percutaneous devices, maxial facial reconstruction plating, dental implants, intraocular lenses, clips, sternal wires, bone, orthopedic prostheses, skin, ligaments, tendons, and combinations thereof.

Percutaneous devices include, without limitation, catheters of various types, cannulas, drainage tubes such as chest tubes, intra-aortic balloons, surgical instruments such as forceps, retractors, needles, and gloves, and catheter cuffs. Catheters can be used for accessing various bodily systems such as the vascular system, the gastrointestinal tract, or the urinary system. Some catheters, such as Hickman catheters, are designed to dwell for extended periods of time within a patient Cutaneous devices include, without limitation, skin grafts, burn dressings, wound dressings of all types, contact lenses and dental hardware, such as bridge supports and bracing components.

While the diamond-like carbon coated polymer materials can be used in any of the medical articles described above, some medical devices are of particular interest. Such devices of particular interest include, for example, implantable vascular devices and implantable cardiovascular devices. Implantable vascular devices include, for example, vascular stents, intra-aortic balloons, vascular grafts and conduits and valved grafts. Implantable cardiovascular devices include, for example, coronary stents, ventricular assist devices with or without valves, and valved cardiovascular prostheses, such as heart valve prostheses, heart valve grafts, and artificial hearts. Some heart valve prostheses are formed mostly from tissue, i.e., bioprosthetic heart valves. Other heart valve prostheses, i.e., mechanical heart valves, are made from components each formed from metal, pyrolytic carbon and/or ceramics, and optionally polymeric components. Diamond-like-carbon coated materials are particularly suitable for use as rigid occluders or flexible leaflets in heart valve prostheses.

Figure 1:
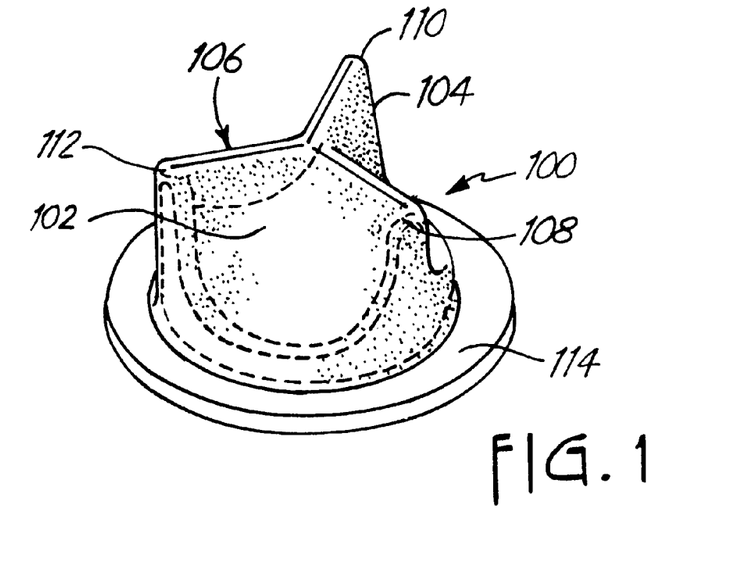
FIG. 1 is a perspective view of a heart valve prosthesis having flexible polymer leaflets coated with diamond-like carbon.
Figure 2:
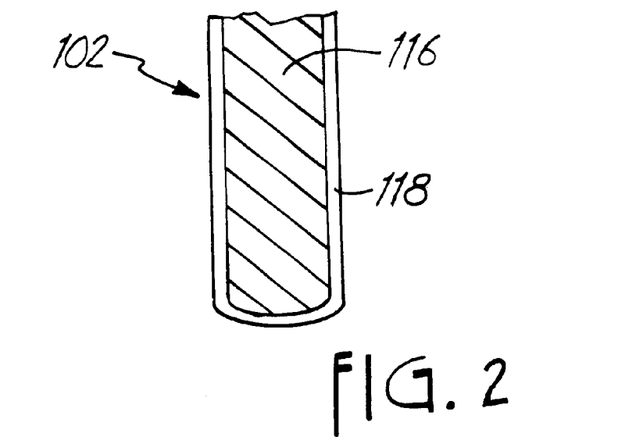
FIG. 2 is a fragmentary, schematic view of a cross section of a polymer leaflet with a diamond-like carbon coating, where the coating thickness is exaggerated for illustration purposes.

An embodiment of a heart valve prosthesis with flexible polymer leaflets or occluders is shown in FIG. 1. Heart valve prosthesis 100 includes leaflets 102, 104, 106 joined at commissures 108, 110, 112, and sewing ring 114. Sewing ring 114 is used to attach valve 100 to patient tissue with sutures, adhesives or other attachment mechanisms. A partial cross section of leaflet 102 is shown in FIG. 2, in which a flexible polymer substrate 116 is coated with a diamond-like carbon coating 118. While the heart valve prosthesis in FIG. 1 is shown with three polymer leaflets, prostheses can be constructed with different numbers of polymer leaflets, such as two leaflets.

A flexible polymer leaflet used to form the leaflets of heart valve prosthesis 100 is preferably a polymer that has sufficient durability to withstand the repeated cycling required for replacement heart valve use. The valve must cycle about 40 million times each year, and the valve ideally must remain functional over the remaining natural expected lifetime of the patient. Depending on the age of the patient at implantation, this natural lifetime may range from about 10 years in an elderly patient to about 60 years to even about 100 years in a young patient. Current tissue valves may require replacement following about 400 million to about 600 million cycles. Therefore, the polymer substrate preferably can withstand at least about 400 million cycles and more preferably can withstand more than about 600 million cycles without significant structural failure. Only a few classes of flexible polymers are believed capable of such performance requirements. Polyurethanes are one of these classes.

Figure 3:
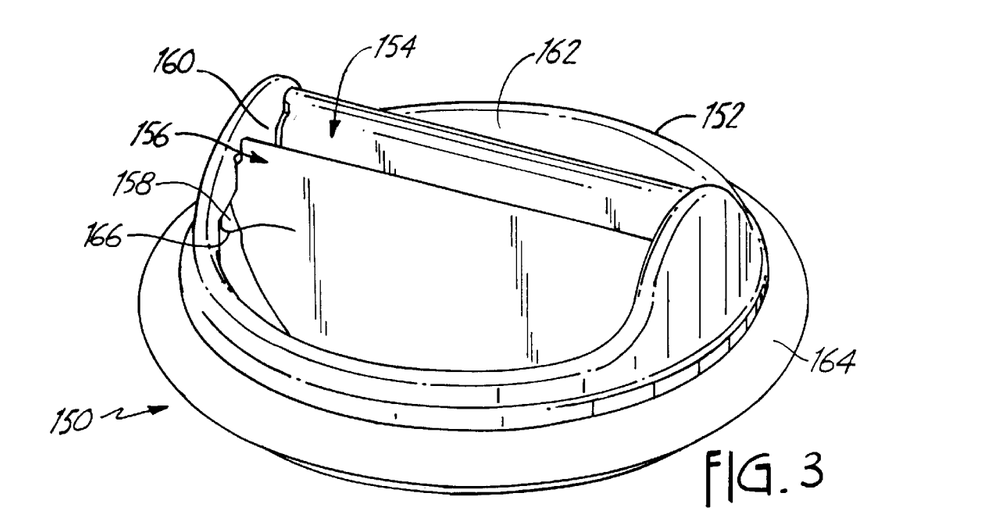
FIG. 3 is a perspective view of a bi-leaflet mechanical heart valve prosthesis with occluders and an orifice ring having a diamond-like carbon coating.

A bi-leaflet mechanical heart valve prosthesis 150 is shown in FIG. 3. Heart valve prosthesis 150 includes an orifice ring 152 with two occluders or leaflets 154, 156. Occluders 154, 156 rotate at pivots 158, 160 and two additional pivots directly opposite (not shown) on the inner surface 162 of ring 152. Inner surface 162 of ring 152 forms a flow path through the valve that can be opened or closed through the pivoting of occluders 154, 156. A sewing cuff 164 is placed around ring 152 to attach valve 150 to patient tissue. Sewing cuff 164 can be formed from a polymer fabric coated with a diamond-like carbon coating.

Occluders 154, 156 can be formed from a rigid polymer substrate covered with a diamond-like carbon coating. Preferably, the surfaces of occluders 154, 156 are entirely covered with a diamond-like carbon coating. It may be sufficient to apply the diamond-like carbon coating to some surfaces of occluders 154, 156, such as surface 166 on occluder 156 and the corresponding surface on occluder 154. In addition, all or a portion of ring 152 can be formed from a rigid polymer, and inner surface 162, for example, can include a diamond-like carbon coating. Alternatively, the entire surface of ring 152 can include a diamond-like carbon coating.

Figure 4:
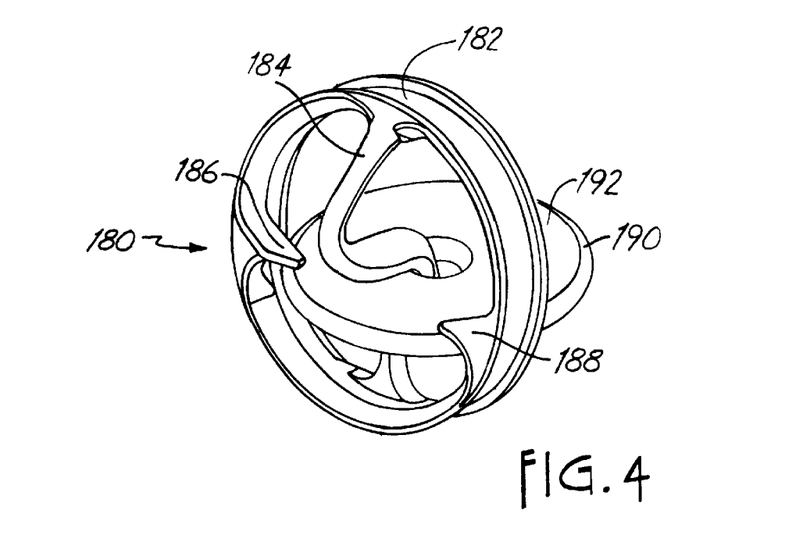
FIG. 4 is a perspective view of a single occluder mechanical heart valve prosthesis with an occluder and orifice ring having a diamond-like carbon coating.

A single-occluder mechanical heart valve prosthesis 180 is shown in FIG. 4. Heart valve prosthesis 180 includes an orifice ring 182 with a pivot arm 184 and two stops 186, 188. Occluder 190 can swing on pivot arm 184 to move between a closed position and an open position as shown in FIG. 4. At a fully open position, the swinging motion of occluder 190 is halted by stops 186, 188. Occluder 190 can be formed from a rigid polymer with a diamond-like carbon coating. Alternatively, only some of the surface of occluder 190 can include a diamond-like carbon coating, such as surface 192 of occluder 190. Similarly, all or portions of ring 182 can be formed from a rigid polymer, of which all or a portion of the surfaces of ring 182 can include a diamond-like carbon coating.

Biocompatible Materials

Relevant medical articles can include one or more biocompatible materials. The medical devices of interest include at least a component comprising the diamond-like carbon coated polymer materials described herein. Other portions of the medical devices that are designed to contact the patient's bodily fluids and/or tissues may include biocompatible materials in addition to the diamond-like carbon coated polymer substrate, such as tissue or tissue derived material, uncoated polymers, metals, pyrolytic carbon, ceramics and combinations thereof, within the same component as the diamond-like carbon coated polymer material or in separate components. While the coating of a component can be performed following the assembly of a multiple component medical device, the coating of a single component within the medical device generally would be performed prior to assembly of the components to avoid interference with the coating process by the other components. Thus, some materials can be incorporated into the medical device that may not be able to withstand the conditions used to form the diamond-like carbon coating.

Appropriate biocompatible materials can be formed from natural materials, synthetic materials or combinations thereof. Natural, i.e., biological, material for use in the invention includes relatively intact living tissue, decellularized tissue and recellularized tissue. These tissues may be obtained from, for example, natural heart valves, portions of natural heart valves such as aortic roots, walls and leaflets, pericardial tissues, such as pericardial patches, connective tissues, tendons, ligaments, skin patches, blood vessels, cartilage, dura mater, skin, bone, fascia, submucosa, umbilical tissues, and the like.

Natural tissues are derived from a selected animal species, typically mammalian, such as human, bovine, porcine, seal, equine, canine or kangaroo. These natural tissues generally include collagen-containing material. Tissues can be fixed by crosslinking. Fixation provides mechanical stabilization, for example, by preventing enzymatic degradation of the tissue. Glutaraldehyde or formaldehyde is typically used for fixation, but other fixatives can be used, such as other difunctional aldehydes, epoxides, genipin and derivatives thereof.

Relevant synthetic materials include, for example, polymers, metals and ceramics. Appropriate ceramics include, without limitation, hydroxyapatite, alumina and pyrolytic carbon. Ceramics can be coated with a polymer, protein or other compound prior to use, if desired. Suitable biocompatible metals include, for example, titanium, cobalt, stainless steel, nickel alloys, iron alloys, cobalt alloys, such as Elgiloy®, a cobalt-chromium-nickel-molybdenum-iron alloy, and MP35N, a nickel-cobalt-chromium-molybdenum alloy, and Nitinol®, a nickel-titanium alloy. For example, ring 152 of bi-leaflet heart valve 150, shown in FIG. 3, can be completely or partially made from metal, while occluders 154, 156 are made from a rigid polymer with a diamond-like carbon coating. Appropriate synthetic materials also include hydrogels and other synthetic materials that cannot withstand severe dehydration.

Biocompatible materials can be fabricated from synthetic polymers as well as purified biological polymers. These synthetic polymeric materials can be formed into fibers and/or yarn and then woven or knitted into a mesh to form a matrix or similar structure. Alternatively, the synthetic polymer materials can be molded, extruded, dip coated or cast into appropriate forms.

Appropriate synthetic polymers include, for example, polygamies (e.g., nylon), polyesters, polystyrenes, polyacrylates, vinyl polymers (e.g., polyolefins, polyethylene, polytetrafluoroethylene, polypropylene, ethylene-propylene copolymers, ethylene-propylene-diene monomer copolymer (FPDM) and polyvinyl chloride), polycarbonates, polyurethanes, polydimethyl siloxanes, cellulose acetates, polymethylmethacrylates, ethylene vinylacetates, polysulfones, polyacetals, nitrocelluloses and similar copolymers. Conductive polymers include, for example, doped polymers of poly(sulfur nitride), polyacetylene, poly(p-phenylene), poly(phenylene sulfide) and polypyrrole. Other suitable polymers include resorbable polymers such as dextran, hydroethyl starch, derivatives of gelatin, polyvinylpyrrclidone, polyvinylalcohol, poly[N-(2-hydroxylpropyl) methacrylamide], polyglycols, polyesters, poly(orthoesters), poly(ester amides), polyanhydrides. Resorbable polyesters include, for example, poly(hydroxy acids) and copolymers thereof, poly($\epsilon$-caprolactone), poly (dimethyl glycolic acid), and poly(hydroxy butyrate). Preferred resorbable polymers include, for example, D, L-polylactic acid, L-polylactic acid, poly(glycolic acid), and copolymers of L-lactic acid, D-lactic acid and glycolic acid. For example, sewing cuff 164 of bi-leaflet heart valve prosthesis 150 of FIG. 3 can be formed to include a resorbable fabric.

Biological polymers can be naturally occurring or produced in vitro by fermentation and the like. Purified biological polymers can be appropriately formed into a substrate by techniques such as weaving, knitting, casting, molding, extrusion, cellular alignment and magnetic alignment. For a description of magnetic alignments see, for example, R. T. Tranquillo et al., Biomaterials 17:349–357 (1996). Suitable biological polymers include, without limitation, collagen, elastin, silk, keratin, gelalin, polyamino acids, cat gut sutures, polysaccharides (e.g., cellulose and starch) and copolymers thereof.

Polymer Substrates

The composite materials described herein include a diamond-like carbon coating over a polymer substrate. Suitable polymeric materials can be fabricated from synthetic polymers as well as purified biological polymers. The polymeric materials can be woven into a mesh to form a matrix or substrate. Alternatively, the synthetic polymer materials can be molded, extruded, dip coated or cast into appropriate forms.

Flexible synthetic polymers are generally referred to as elastomers and rigid synthetic polymers are generally referred to as plastics. Appropriate synthetic polymers include, without limitation, polygamies (e.g., nylon), polyesters, polystyrenes, polyacrylates, vinyl polymers (e.g., polyolefins, polyethylene, polytetrafluoroethylene or other halogenated polymers, polypropylene, ethylene-propylene copolymers, ethylene-propylene-diene monomer copolymer (EPDM) and polyvinylchloride), polycarbonates, polyacetals (e.g., Delrin®), polyurethanes, polydimethyl siloxanes, cellulose acetates, polymethylmethacrylates, ethylene vinyl acetates, polysulfones, nitrocelluloses, polyetheretherketones (PEEK) and similar copolymers. Conductive polymers include, for example doped polymers of poly(sulfur nitride), polyacetylene, poly(p-phenylene), poly(phenylene sulfide) and polypyrrole.

Biological polymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment. For a description of magnetic alignments see, for example, R. T. Tranquillo et al., Biomaterials 17:349–357 (1996). Suitable biological polymers include, without limitation, collagen, elastin, silk, keratin, gelatin, polyamino acids, cat gut sutures, polysaccharides (e.g., cellulose and starch) and copolymers thereof.

Preferred polymers are biocompatible. For preferred applications the polymer substrates are thin. For flexible embodiments, the polymer substrates generally have a thickness from about 10 microns to about 600 microns and more preferably from about 50 microns to about 300 microns. For rigid embodiments of particular interest, the polymer substrates have a thickness less than about 1500 microns, preferably from about 100 microns to about 1200 microns and more preferably from about 200 microns to about 800 microns.

Polymers can be flexible or rigid depending on their composition and final form, including thickness. Flexible polymers include elastomers and other polymers that can sustain significant flexure, bending, twisting and/or deformation without structural failure. Particularly preferred flexible polymer materials for the application of a diamond-like carbon coating include, for example, polyurethanes, polydimethyl siloxane and polytetrafluoroethylene. Preferred rigid polymers for the application of a diamond-like carbon coating include, for example, polysulfone, polyacetal, polyethersulfone, polyarylsulfone, polyetheretherketone, and polyetherimide.

Diamond-Like Carbon Coated Polymer Materials

The diamond-like carbon coating is applied over all or a portion of a polymer substrate. The diamond-like carbon can be applied by various low pressure deposition approaches, as described further below. Diamond-like carbon coatings possess a variety of desirable characteristics related to the hardness and inertness of the material.

Diamond-like carbon coatings yield an electron diffraction image with a halo pattern and a Raman vibrational spectrum with broad peaks indicative of inhomogeneous broadening due to an amorphous structure centered at frequencies of 1580 $cm^{-1}$ and 1360 $cm^{-1}$. Typical ranges of selected properties of several forms of carbon materials at 25° C. are presented in Table 1.

TABLE 1*

| Carbon Form | Density (g/cm$^3$) | Young's modulus (GPa) | Hardness (kg/mm$^2$) | Thermal Conductivity (W/mK) |
| --- | --- | --- | --- | --- |
| DLC | 1.6–2.8 | 45+ | 800–9000 | 100–1000 |
| Pyrolytic Graphite, oriented | 2.1–2.2 | 28–40 | 240–370 | 190–390 (ab directions) 1–3 (c direction) |
| Vitreous | 1.5 | 35 | 340 | 4.6 |
| Graphite | 1.7–1.9 | 5–10 | 40–100 | 31 (lamp black) 159 (petrol coke) |
| Diamond | 3.5 | 910–1250 | 5000–10,000 | 600–1000 (Type 1a) |

*See Handbook of Carbon, Graphite, Diamond and Fullerenes: Properties, Processing and Application, by Hugh O. Pierson, Noyes Publication, Park Ridge, New Jersey, U.S.A. (1993), incorporated herein by reference.

However, some diamond-like carbon materials produced by ion beam assisted deposition can have a hardness value higher than those shown for diamond-like carbon in Table 1.

Diamond-like carbon coatings for flexible polymer substrates are composed of a majority of carbon atoms with a significant amount of hydrogen, generally less than about 45 atomic percent hydrogen, preferably from about 15 to about 40 atomic percent, and more preferably from about 25 atomic percent to about 40 atomic percent hydrogen. Diamond-like carbon coatings for rigid polymer substrates preferably have from about 5 atomic percent to about 40 atomic percent hydrogen and more preferably from about 10 atomic percent to about 30 atomic percent hydrogen. The formation of coatings with a desired degree of hardness depends on appropriate quantities of hydrogen atoms in the structure. In addition, diamond-like carbon coatings can contain smaller amounts of other elements. For example, the diamond-like carbon coating can include up to about 5 atomic percent of oxygen or nitrogen as well as small quantities of other materials.

As noted above, for the production of flexible components, the diamond-like carbon coating will be flexible so that the flexural properties of the substrate polymer material will not be altered significantly. More flexible diamond-like carbon coatings for application to flexible polymer components have larger proportions of hydrogen and, therefore, lower densities. These flexible diamond-like carbon coatings generally are on the lower end of the hardness scale for diamond-like carbon coatings. Preferred diamond-like carbon coatings for rigid polymer substrates are harder due to lower proportions of hydrogen and correspondingly higher densities.

In some embodiments, as described further below, the diamond-like carbon coating is applied under conditions in which the coating is chemically bonded to the underlying polymer substrate. In particular, carbon-carbon bonds are formed between carbon atoms of the coating and carbon atoms of the organic polymer. This bonding of the coating to the substrate greatly improves adhesion of the coating to the substrate since an integral structure is formed.

The diamond-like carbon coating thickness is measured along the normal (perpendicular) to the polymer substrate surface. The thickness normal to the polymer surface may be determined using a witness piece that is sectioned to expose the interface. This method is applicable even if the diamond-like carbon coating penetrates the polymer surface. The use of a witness piece for thickness evaluation is described further below. Generally, the diamond-like carbon coatings are applied in a thickness from about 10 nm to about 10 microns ($\mu$m), preferably from about 50 nm to about 2 $\mu$m and more preferably from about 250 nm (0.25 $\mu$m) to about 1.0 $\mu$m. In particular, for a flexible polymer substrate, the diamond-like carbon coating even more preferably has a thickness from about 100 nm to about 500 nm. Similarly, for a rigid polymer substrate, the diamond-like carbon coating even more preferably has a thickness from about 250 nm to about 800 nm.

For coatings transparent to ultraviolet, visible and/or infrared light, thickness can be measured, for example, using optical reflectometry or ellipsometry, as described in "Spectroscopic Ellipsometry and Reflectometry: A User's Guide," by H. G. Tompkins and W. A. McGahan, (John Wiley & Sons, Inc., 1999), incorporated herein by reference. In reflectometry, the intensity of a beam of light, generally monochromatic, is measured before and after it reflects from the coating. The ratio of intensities is a measure of coating thickness. Alternatively, the ratio can be taken of the intensity of reflected light from a standard mirror and from the coating.

In ellipsometry, linearly polarized light is reflected from the coating at one or more angles of incidence. Reflection of the beam causes the light to become elliptically polarized. The degree of elliptical polarization is measured, for example, with a rotating polarizing filter. The degree of elliptical polarization provides information on the coating thickness. The measurement of coating thickness using ellipsometry is further described in ASTM procedure F576-

90 (published November 1990), incorporated herein by reference. The ASTM method uses a polarized, monochromatic light source and optical components to direct the light toward the coating surface. The reflected light undergoes a change in azimuthal angle and degree of elliptical polarization that is measured to determine the thickness.

Alternatively, thickness can be measured by applying a diamond-like carbon coating under the same conditions to a witness piece that can be destructively examined to evaluate thickness. For example, the coating thickness of a witness piece can be evaluated by cutting a cross section and examining the cross section with an electron microscope or by reflectometry, ellipsometry or profilometry. By applying equivalent coatings using the same procedure used to apply the coating to the witness piece, it is assumed that the coating thickness will be the same as that measured with the witness piece.

As noted above, all or a portion of the substrate can be covered with a diamond-like carbon coating. For example, a diamond-like carbon coating can be applied as an approximately uniform coating over a desired section or the entire surface of the substrate. In some preferred embodiments, a uniform coating is identifiable as a coating in which the thickness at all points along the substrate varies by less than about 50% and more preferably less than about 10% relative to the average coating thickness. Of course, if the diamond-like carbon coating does not cover the entire substrate, the edge of the coating forms a discontinuity. The presence of an edge is not considered to result in a non-uniform coating.

Alternatively, the diamond-like carbon coating can be applied in a non-uniform coating such that the thickness of the coating varies at different regions of the substrate. In some embodiments, it may be desirable for the maximum coating thickness to be more than a factor of about two (2) thicker than the minimum coating thickness. Application of a non-uniform coating can accomplish a variety of goals including simplifying deposition, adding mechanical stability to stress points or locations and/or altering the geometry of the component/device. In particular, for rigid polymer substrates, the diamond-like carbon coating can be thicker at portions of the substrate that are expected to be subjected to high stress or wear since the diamond-like carbon coating can provide increased fatigue and wear/tear resistance. Also, the thickness of a diamond-like carbon coating over high stress areas of a flexible polymer substrate may be increased to give higher assurance of coverage, i.e., to reduce the risk of gaps in the coating. A thicker coating may also provide increased tear resistance. The deposition approach may inherently produce a diamond-like carbon coating that is non-uniform in thickness unless significant efforts are made to reduce the non-uniformity.

Furthermore, the composition of the diamond-like carbon coating can have a uniform composition or the composition can vary at different regions of the coating. For example, regions subject to applied stress levels after implant can have a particular diamond-like carbon coating composition while other portions of the coating can be formed with other dopants, for example, to vary the flexibility. Similarly, the diamond-like carbon coating can have layers of diamond-like carbon with different compositions. Non-uniform and/or layered compositions can be introduced by the deposition approaches described further below.

Application of Diamond-Like Carbon Coating

It is important that the polymer substrate does not undergo significant structural or chemical degradation as a result of the deposition of the diamond-like carbon coating. Thus, the diamond-like-carbon coating should be applied with a suitable deposition technique and under conditions at which the underlying polymer substrate is not significantly degraded structurally or chemically. In particular, the bulk or overall properties of the polymer preferably do not change significantly even though there may be changes at the interface between the diamond-like carbon coating and the polymer. While the polymer substrate can be selected to have better stability with respect to standard deposition conditions, there are limitations on the stability of polymers under harsh conditions involving heat and reactive chemical species such as ionic vapors.

Methods for the deposition of thin film diamond-like carbon coatings generally involve very low pressures. For example, carbon coatings can be applied by vacuum techniques, such as sputtering and magnetron sputtering, and other physical vapor deposition methods. Suitable dopants can be introduced by including the desired elements in the precursor compounds or by introducing a background vapor with the desired elements. Diamond-like carbon coatings can be produced, for example, by chemically assisted physical vapor deposition from hydrocarbon-containing gases, such as plasma enhanced chemical vapor deposition (PE-CVP).

In preferred embodiments, more sophisticated approaches are used to deposit the diamond-like carbon where the conditions can be controlled more precisely. Preferred approaches generally have assisted deposition where the substrate is mounted on a stage and ionic beams are used to form the coating from a precursor at the surface. Preferred approaches include, for example, ion beam assisted deposition.

Ion beam assisted deposition is a particularly preferred approach for the deposition of a diamond-like carbon coating onto polymer substrates. Ion beam assisted deposition is performed under high vacuum as described, for example, in U.S. Pat. No. 5,474,797 to Sioshansi et al., incorporated herein by reference. U.S. Pat. No. 5,725,573 to Dearnaley et al., entitled "Medical Implants Made Of Metal Alloys Bearing Cohesive Diamond Like Carbon Coatings," incorporated herein by reference, describes the deposition of a diamond-like carbon coating onto metal or ceramic substrates using ion beam assisted deposition. The ion beam assisted deposition generally is performed within a chamber formed, for example, from stainless steel or glass.

To deposit a diamond-like carbon coating onto a polymer substrate, the substrate may be mounted onto a stage or placed within a metal or polymer wire cage. The substrate is not heated overall. However, the coating deposition generally heats the surface of the substrate. Generally, the substrate surface temperature is heated to a temperature less than about 200° C., and in some preferred embodiments less than about 150° C. In other embodiments, the polymer substrate preferably reaches a temperature at its surface during the coating process below about 100° C., such that heat sensitive polymer substrates are not melted or degraded during the coating process. The coating process should be performed such that the temperature reached by the polymer substrate does not degrade the polymer. Thus, the polymer substrate preferably is not structurally or chemically degraded to a significant degree, i.e., the mechanical and chemical properties of the bulk polymer substrate of the component following deposition is not altered.

The stage or the wire cage preferably is movable such that different portions of the substrate can be placed in the path of an ion beam for the formation of the coating.

Alternatively, the coating process can be stopped to reorient the substrate such that a different portion of the substrate can be the target of the ion beam.

The deposition is performed at a base pressure on the order of $10^{-4}$ Torr or less, prior to the introduction of the precursor composition. An organic precursor is used to form the diamond-like carbon coating in the ion beam assisted deposition approach. Suitable organic precursors include compounds that have a low vapor pressure at room temperature and can be vaporized without breaking down at a higher temperature, such as about 150° C. to about 200° C. Carbon based diffusion pump oils, for example, polyphenylether, polydimethylsiloxane, pentaphenyltrimethylsiloxane and elcosylnaphthalene, have these preferred properties. The precursor is condensed onto the surface to be coated, for example, by evaporating the precursor near the polymer surface.

Essentially simultaneously with the condensation of the precursor, the surface is bombarded with the ion beam to fragment the precursor molecules and release at least hydrogen from the composition. For standard precursors, the ionization fragments roughly 80% or more of the carbon-hydrogen bonds to form the diamond-like carbon coating. The ions within the ion beam generally have an energy between about 500 eV and 100 keV, and preferably from about 1 keV to about 15 keV for flexible polymer substrates and preferably from about 3 keV to about 25 keV for rigid polymer substrates. Generally, a lower beam voltage is correlated with a higher concentration of hydrogen in the coating.

The rate of ion bombardment preferably is correlated with the rate of precursor delivery for a more efficient process. The preferred rate of ion bombardment will vary depending on the identity of the ions and precursor and on the processing conditions. The deposition process is continued until a desired coating thickness is reached. Preferably, the diamond-like carbon coating is formed with chemical bonds to the underlying polymer substrate, such that the coating is strongly adhered to the substrate and generally will not separate from the substrate.

Properties of Diamond-like Carbon Coated Polymer Materials

The diamond-like carbon coating have a variety of properties that make the coated components particularly suitable for use in medical devices. In particular, the hardness and smoothness of the surface provide the coated components with excellent biocompatible and blood compatible properties. The diamond-like carbon coating is resistant to corrosion and other forms of surface modification. Thus, the coated components can be used advantageously in prostheses for the cardiovascular system. Also, the chemical inertness and impermeability of diamond-like carbon coatings result in a resistance to calcification and other chemical modification due to prolonged exposure to a patient's bodily fluids. The hardness and inertness result in a durable product which generally does not undergo structural degradation over reasonable periods of time.

Completion of the Medical Device, Storage, Packaging, Distribution and Use

The diamond-like carbon coated polymer substrate can form an entire medical device itself, or the coated substrate can be incorporated with other biocompatible components into a medical device. For example, a diamond-like carbon coated polymer substrate forming a heart valve leaflet can be incorporated into a heart valve prosthesis, prior to storage and/or distribution of the resulting prosthesis. While the coating of a component can be performed following the assembly of a multiple component medical device, the coating of a single component within the medical device generally would be performed prior to assembly of the components to avoid interference with the coating process by the other components.

The diamond-like carbon coated polymer can be stored appropriately prior to or following formation into a medical device. Generally, the coated polymer material would be stored in a dry, sterile environment. If components of the medical device require moisture to maintain their integrity, such as tissue components, the medical device with the diamond-like carbon coated polymer composite can he stored in a moist, sterile environment. The moist environment can be maintained with or without immersing the medical device in a sterile liquid, such as aqueous glutaraldehyde.

For distribution, the medical devices are placed in sealed and sterile containers. The containers can be dated such that the date reflects the maximum advisable storage time, if components of the medical device should not be stored indefinitely. The containers are packaged along with instructions for the proper use and/or implantation of the medical device and along with other appropriate and/or required labeling. The containers are distributed to health care professionals for use in appropriate medical procedures, such as implantation of a prosthesis and the like.

The embodiments described above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What ia claimed is:

1. A medical article suitable for contact with a patient's blood, the medical article comprising a polymer substrate at least a portion of which is coated with a diamond-like carbon coating having a thickness from about 10 nm to about 2 microns, the medical article being a heart valve prosthesis capable of more than about 100° bending.

2. The medical article of claim 1 wherein the polymer substrate comprises a flexible polymer.

3. The medical article of claim 1 wherein the polymer substrate comprises polyurethane, polyacetal, ethylene-propylene copolymers, polytetrafluoroethylene, polysulfone, polyethersulfone, polyarylsulfone, polyetheretherketone, polydimethylsiloxane, or polyetherimide.

4. The medical article of claim 1 wherein the polymer substrate comprises polyurethane.

5. The medical article of claim 1 wherein the diamond-like carbon coating is covalently bonded to the polymer substrate.

6. The medical article of claim 1 wherein the diamond-like carbon coating comprises less than about 45 atomic percent hydrogen.

7. The medical article of claim 1 wherein the diamond-like carbon coating comprises from about 15 atomic percent to about 40 atomic percent hydrogen.

8. The medical article of claim 1 wherein the diamond-like carbon coating has a thickness greater than about 250 nm.

9. The medical article of claim 1 wherein the diamond-like carbon coating is uniform over the coated portion of the polymer substrate.

10. The medical article of claim 1 wherein the heart valve prosthesis comprises leaflets and the leaflets of the heart valve prosthesis comprise the polymer substrate with a diamond-like carbon coating.

11. The medical article of claim 1 wherein the polymer substrate has a thickness less than about 800 microns.

12. The medical article of claim 1 wherein the polymer substrate has a thickness less than about 600 microns.

13. A heart valve prosthesis comprising at least one component, the at least one component comprising a polymer substrate at least partially coated with diamond-like carbon and wherein the diamond-like carbon coating has a thickness of from about 10 nm to about 2 microns and is chemically bonded to the polymer substrate.

14. The heart valve prosthesis of claim 13 wherein the at least one component comprises a leaflet.

15. The heart valve prosthesis of claim 13 wherein the at least one component comprises an orifice ring.

16. The heart valve prosthesis of claim 13 wherein the at least one component comprises a sewing cuff.

17. The heart valve prosthesis of claim 13 wherein said polymer substrate has a thickness of less than about 1500 microns.

18. The heart valve prosthesis of claim 13 wherein said diamond-like coating has a thickness of from about 250 nm to about 1 micron.

19. The heart valve prosthesis of claim 13 wherein said heart valve prosthesis being capable of more than about 100° bending.

20. The heart valve prosthesis of claim 13 wherein said diamond-like coating comprises from about 15 to about 40 atomic percent hydrogen.

21. A medical article suitable for contact with a patient's bodily fluids, the medical article comprising a polymer substrate at least a portion of which is coated with a diamond-like carbon coating, the polymer substrate having a thickness less than about 600 microns.

22. The medical article of claim 21 wherein the polymer substrate is flexible.

23. The medical article of claim 21 wherein the polymer substrate comprises polyurethane.

24. The medical article of claim 21 wherein the diamond-like carbon coating has a thickness from about 10 nm to about 10 microns.

25. The medical article of claim 21 wherein the diamond-like carbon coating has a thickness greater than about 250 nm.

26. The medical article of claim 21 wherein the medical article comprises a heart valve prosthesis.

27. The medical article of claim 26 wherein the leaflets of the heart valve prosthesis comprise the polymer substrate with a diamond-like carbon coating.

28. The medical of claim 21 wherein the polymer substrate has a thickness from about 50 microns to about 300 microns.

29. The medical device of claim 21 wherein said diamond-like carbon coating is chemically bonded to the polymer substrate.

* * * * *